US012797103B2

(12) United States Patent
Schweinberger et al.

(10) Patent No.: US 12,797,103 B2
(45) Date of Patent: Nov. 17, 2026

(54) HANDHELD SURGICAL INSTRUMENT

(71) Applicant: OLYMPUS WINTER & IBE GMBH, Hamburg (DE)

(72) Inventors: Henning Schweinberger, Basthorst (DE); Hannes Miersch, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 298 days.

(21) Appl. No.: 18/414,202

(22) Filed: Jan. 16, 2024

(65) Prior Publication Data

US 2024/0315721 A1 Sep. 26, 2024

Related U.S. Application Data

(60) Provisional application No. 63/454,116, filed on Mar. 23, 2023.

(51) Int. Cl.
*A61B 17/32* (2006.01)
*A61B 17/00* (2006.01)

(52) U.S. Cl.
CPC ................. *A61B 17/320016* (2013.01); *A61B 2017/00867* (2013.01)

(58) Field of Classification Search
CPC .............. A61B 17/320016; A61B 2017/00867
See application file for complete search history.

(56) References Cited

U.S. PATENT DOCUMENTS

| | | | | |
|---|---|---|---|---|
| 5,665,050 A * | 9/1997 | Benecke | A61B 17/29 | 148/563 |
| 2007/0250113 A1* | 10/2007 | Hegeman | A61B 1/0055 | 606/207 |
| 2013/0030462 A1* | 1/2013 | Keating | A61B 17/29 | 606/206 |
| 2015/0351792 A1* | 12/2015 | Houser | A61B 17/320092 | 606/171 |
| 2018/0344427 A1* | 12/2018 | Rosenbaum | A61B 90/70 | |
| 2021/0235970 A1 | 8/2021 | Graveley et al. | | |

FOREIGN PATENT DOCUMENTS

DE 4411099 C2 7/1998

OTHER PUBLICATIONS https://customwiretech.com/2021/07/the-nitinol-advantage/ (Year: 2021).*

* cited by examiner

*Primary Examiner* — Niketa Patel
*Assistant Examiner* — Sebastian X Lukjan
(74) *Attorney, Agent, or Firm* — Oliff PLC

(57) ABSTRACT

A handheld surgical instrument that can be cleaned in a particularly simple, thorough and time-efficient manner. This is achieved by the fact that the instrument has at least one first component and at least one second component. The first component can be, for example, a cap, a cover or the like. The second component can be designed as a connection, connection body, optical guide plate or the like. The two components are movable relative to each other and can be coupled to each other by screwing or the like. A structural element made from a shape-memory material is arranged between these two components. This shape-memory material makes it possible to achieve a temperature-dependent relative arrangement of the two components.

8 Claims, 3 Drawing Sheets

HANDHELD SURGICAL INSTRUMENT

The invention relates to a handheld surgical instrument according to the preamble of claim 1. The invention further relates to a handheld surgical instrument according to claim 6.

Handheld surgical instruments, such as endoscopes, resectoscopes, forceps or the like, are mainly used for endoscopic applications in urology or gynecology, preferably for treatment in the region of the bladder, uterus or prostate. However, the field of application of these instruments is not limited to these regions of the human body and instead includes the treatment of other organs in the human abdomen.

The instruments of the type described here, such as endoscopes, resectoscopes, forceps or the like, usually have several components that are movable relative to one another. In addition, the instruments of the type in question are assembled from various components that are screwed or clicked together. As an example of such an instrument, the structure of an instrument of the type in question, namely a resectoscope, will be briefly outlined below.

Resectoscopes routinely have a working element. To treat diseased tissue, the resectoscope is inserted with an elongate shaft through an opening into the patient's body. Various medical instruments for the treatment and/or examination of the patient can be arranged in this shaft tube. For example, for radiofrequency surgery, an electrode positioned at a distal end of an electrode carrier and subjected to radiofrequency alternating current can be guided through the shaft. For the manipulation or cutting of the tissue, the electrode carrier with the electrode is movable relative to the shaft tube and along a shaft axis such that, by moving the electrode along or through the tissue, the latter is manipulated.

The electrode carrier is also coupled with its proximal end to the working element. This handling of the working element permits the cutting movement of the electrode. The working element has a movably mounted contact body, which is also referred to as a carriage. On this contact body, the electrode carrier can be mechanically and releasably coupled to an electrical contact. The electrode carrier or electrode can also be supplied with electrical energy via this mechanical connection. For this purpose, the contact body has a bore or opening in the form of a blind hole, into which an electrical contact of the electrode carrier for the releasable connection can be guided. This opening or this blind hole is designed in such a way that the RF voltage can be applied via an adjacent connector. This is usually done by inserting a plug into the socket, which plug in turn can be connected to an RF generator via a line or cable.

The actuation or longitudinal displacement of the working element, i.e. also of the electrode, is carried out by an operating surgeon. For this purpose, the working element is assigned a handle unit with a first grip means and a second grip means. To actuate the working element, the operating surgeon grasps the first grip means, and also the second grip means, which can have a finger unit or a thumb ring. The first grip means can be attached to a fixed main body of the working element. The second grip means can be attached to the contact body.

The movement of the working element takes place against a spring tension force of a spring which, in the working element of the type in question, is usually designed as a leaf spring or as a leg spring. This spring is attached with one end to the contact body or carriage and with the other end to an end body or an optical guide plate of a strengthening tube.

The type of springs or the type of actuation of this spring mechanism depends on whether the working element is an active or passive working element. While the spring is designed as a compression spring in an active working element, it is designed as a tension spring in a passive working element.

The shaft of the instruments described here also provides guidance for an optical unit. The rod-like or shaft-like optical unit is guided from the proximal end through a strengthening tube of the working element into the shaft. Exemplary embodiments are known in which the optical unit is guided, as a rod lens system or as a glass fiber, from a proximal end through the shaft to the distal end. The distal end of the optical unit is oriented directly at the region to be operated on or at the site of action of the electrode. At the proximal end of the optical unit, the operating surgeon can observe the treatment through an eyepiece or a camera.

The at least one electrical contact of the electrode system is then connected to the contact body and then pushed through or into the shaft. By actuation of the second grip means relative to the first grip means, the contact body together with the electrode carrier can be moved to and fro along the shaft axis via a strengthening tube.

At the proximal end of the strengthening tube, the latter is welded to an optical guide plate. The contact body is arranged movably on the strengthening tube. For this purpose, the contact body has a corresponding bore for the strengthening tube parallel to the shaft axis. This bore is dimensioned in such a way that the contact body or the carriage can be easily pushed over the strengthening tube.

As has already been mentioned, the resectoscope is cited here only as one of several possible handheld surgical instruments of the type in question. Endoscopes, cystoscopes, forceps or other instruments could equally be mentioned. However, all instruments of the type in question have in common that the necessary cleaning or sterilization before re-use of the instruments or of the individual components is always associated with increased work. Thus, it is almost the rule that mechanical assemblies or several interconnected components have gaps or cavities that are present on account of the functionality of the instruments. These gaps and cavities are given special attention during cleaning and sterilization, since insufficient cleaning or sterilization can lead to spread of germs. Known instruments according to the prior art have assemblies or components that are static and that cannot be brought into a preferred position in order to attain the required thoroughness during cleaning. At best, the components can be dismantled in order to clean the disconnected assemblies or components. However, this is an extremely time-consuming process for the user.

Proceeding from this, the problem addressed by the invention is to make available a handheld surgical instrument that can be cleaned in a particularly simple, thorough and time-efficient manner.

A handheld surgical instrument for solving this problem has the features of claim 1. Accordingly, it is provided that the instrument, which can in particular be an endoscope, a resectoscope or the like, has at least one first component and at least one second component. The first component can be, for example, a cap, a cover or the like. The second component can be designed as a connection, connection body, optical guide plate or the like. The two components are movable relative to each other and can be coupled to each other by screwing or the like. A structural element made from a shape-memory material is arranged between these two components. This shape-memory material makes it possible to achieve a temperature-dependent relative arrangement of the two components. For example, when the instrument or the two components are exposed to elevated temperatures for cleaning or sterilization purposes, in particular to liquid with an elevated temperature, the structural element arranged between the two components changes its geometry, and openings, gaps and lumina form between the components, such that the access to internal cavities can be improved and increased flows of flushing fluid through the gaps can be achieved. When cleaning is completed or the components have cooled down, the structural element returns to its original shape, in which the two components are in their relative working position. By virtue of the arrangement of the structural element made from the shape-memory material, the components for cleaning or sterilization can be brought to a preferred position, so that they can be conditioned in a particularly simple and thorough way. After the process, the components return to their original relative arrangement, specifically without any additional effort on the part of an operator.

Preferably, it is conceivable that this structural element is a wave spring, which is produced, for example, from nitinol. However, it is equally conceivable, that the structural element is produced from another shape-memory material.

In particular, the invention provides that the structural element is maximally compressed at a characteristic temperature of less than 50° C., preferably at room temperature, and a distance between the two components is minimal, and that preferably the two components and the structural element bear on each other without gaps. Likewise, it can be provided according to the invention that the structural element is maximally relaxed at a characteristic temperature of more than 50° C., preferably of 100° C., and there is a gap present between the two components.

A handheld surgical instrument for solving the stated problem has the features of claim 6. Accordingly, it is provided that the instrument, which can be an endoscope, a resectoscope or the like, has at least two components, namely a first component and a second component. These components can be grip parts, parts of a forceps, latching elements, cables, anti-kink means or the like. These two components are movable relative to each other so that the instrument can be brought into different working positions. It is provided that the two components are mechanically coupled to each other by a structural element made from a shape-memory material.

This shape-memory material makes it possible to achieve various temperature-dependent relative orientations or positioning of the two components. For example, if the instrument or the two components are exposed to elevated temperatures for cleaning or sterilization purposes, in particular to liquid with an elevated temperature, the two components move to a preferred relative position, so that the access to internal surfaces and cavities can be improved and increased flows of flushing fluid can be achieved. When cleaning is completed or the components have cooled down, the structural element returns to its original shape, in which the two components are in their relative working position. By virtue of the arrangement of the structural element, the components for cleaning or sterilization can be brought to a particularly favorable relative position, so that they can be conditioned in a particularly simple and thorough way. After the process, the components return to their original relative alignment, specifically without any additional effort on the part of an operator.

According to the invention, it can be provided that the structural element is a spring, in particular a wave spring, a wire mesh, a leg spring or the like. It is conceivable that, for example, the leg spring is connected to the grip parts in order to hold the two grip parts relative to each other in a predetermined position. It is equally conceivable that a wave spring is positioned between two moving components or latching elements. It is equally conceivable that a wire mesh is arranged in a protective sleeve for a cable. The invention also comprises an exemplary embodiment in which a spring holds the elements of a forceps jaw open. In addition, further application examples in connection with the surgical instrument are also conceivable. Nitinol is a particularly preferred material for the structural element.

It is preferably provided that the structural element has a basic shape at a characteristic temperature of less than 50° C., preferably at room temperature, and a relative orientation of the two components corresponds to a working position. At a characteristic temperature of more than 50° C., preferably of 100° C., the structural element relaxes to the maximum extent, and a distance between the two components increases or decreases. On account of this temperature dependence of the shape of the structural element, the components can be brought to a relative position by heating, in which position they can be cleaned in a particularly simple, time-efficient and thorough manner. By simply cooling, i.e. without any further effort by an operator, the structural element or the components return to their position in which they are available for further work.

A preferred exemplary embodiment of the invention is explained in more detail below with reference to the drawing, in which.

Figure 1:
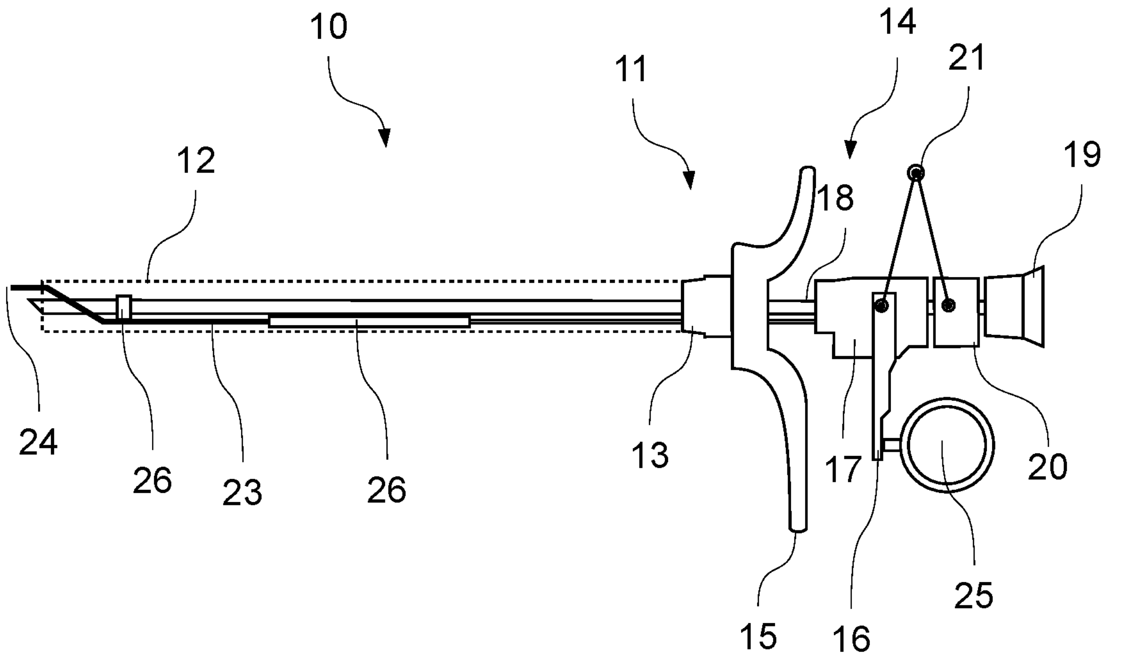
FIG. 1 shows a schematic view of a resectoscope.

An example of a surgical instrument, namely a resectoscope 10, is shown in a highly schematic form in FIG. 1. As has already been mentioned, this resectoscope 10 is merely an example. It is expressly emphasized that the claimed instruments can also be other instruments, such as an endoscope, a cystoscope, forceps or the like.

The resectoscope 10 shown here has a working element 11, to which an elongate, tubular shaft 12 can be fastened. This shaft 12 is shown by section lines in FIG. 1 and is fastened with a proximal end to a main body 13 of the working element 11.

The working element 11 has a handle unit 14 in addition to the main body 13. This handle unit 14 has a first grip means 15 and a second grip means 16. Whilst the first grip means 15 is arranged fixedly on the main body 13, in the exemplary embodiment of the working element 11 shown here the second grip means 16 is assigned to a contact body 17. It is conceivable that the second grip means 16 is screwed onto the contact body 17.

The contact body 17 is guided in a sliding manner on a tubular optical guide 18. For this purpose, the contact body 17 has a bore whose diameter is slightly greater than a diameter of the optical guide 18. Since the contact body 17 can be moved back and forth on the optical guide 18 along a longitudinal direction of the resectoscope 10 or a longitudinal axis of the shaft 12, the contact body 17 is also referred to as a carriage.

While the optical guide 18 is connected with a distal end to the main body 13 or an inner tube 22, an optical guide plate 20 is attached to a proximal end of the optical guide 18. The tubular optical guide 18 extends through the optical guide plate 20, so that the optical guide 18 is accessible from the proximal direction.

The second grip means 16 and the contact body 17 are connected to the optical guide plate 20 via a spring element 21. This spring element 21 can be a tension spring or a compression spring, depending on the type of construction of the working element 11.

Starting from the main body 13, a tubular inner tube 22 extends in the distal direction. This inner tube 22 can also extend in the proximal direction through the main body 13 and be connected to the optical guide 18.

An electrode carrier 23 extends parallel to the inner tube 22. This electrode carrier 23 is routed through the main body 13 and is mechanically and releasably coupled with at least one proximal contact to the contact body 17. At a distal end, the electrode carrier 23 has an electrode 24. An electrical RF voltage can be applied to this electrode 24. The diseased tissue can be manipulated or cut by means of thermal energy that forms on the electrode 24. For this purpose, the operating surgeon moves the second grip means 16, having a thumb ring 25, relative to the first grip means 15. To stabilize the electrode carrier 23, the latter can be guided on the inner tube 22 through guides 26.

For performing the operation, a rod-like optical unit is guided through the inner tube 22 or the optical guide 18. A distal end (not shown here) of this optical unit is directed toward the electrode 24, so that the operating surgeon has a view of the manipulation of the tissue. This optical unit can be a rod lens system or a fiber optic. As is shown in FIG. 1, an eyepiece 19 or a camera is located at the proximal end of the optical unit.

Figure 2:
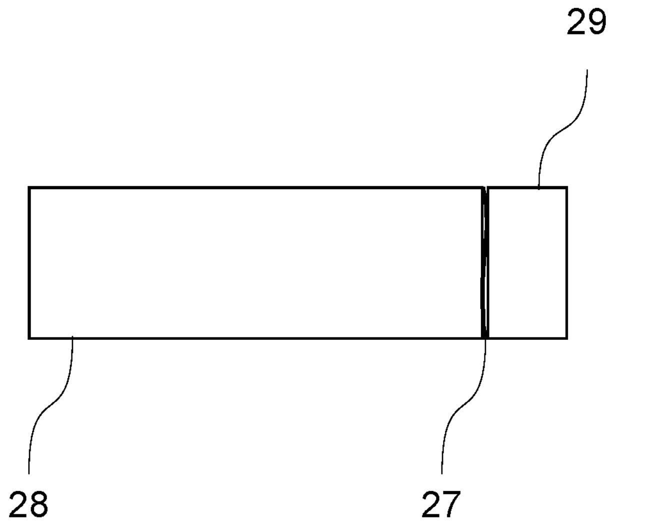
FIG. 2 shows a schematic view of two components in a basic position.
Figure 3:
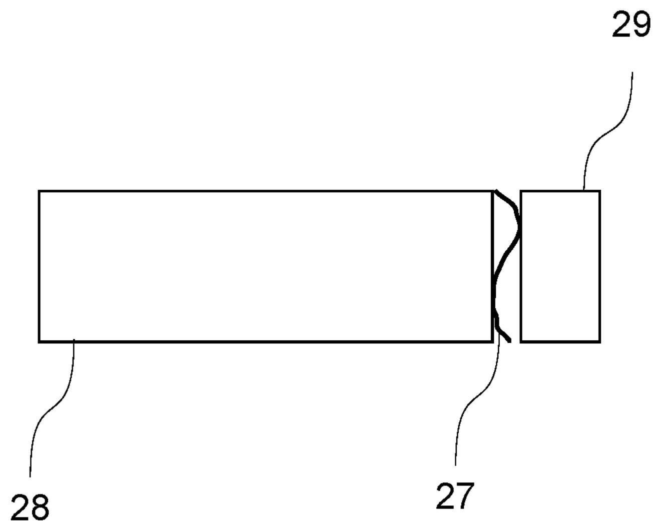
FIG. 3 shows a schematic view of the components according to FIG. 2 in a heated state.

From this broadly outlined description of the structure of the resectoscope 10, it is already clear that surgical instruments of this kind are composed of a large number of components, structural parts or tools. After the treatment, these components etc. have to be cleaned or sterilized with sufficient thoroughness. It has already been noted that this is often only possible with an increased amount of work. Therefore, the invention provides that at least some of the components mentioned above as examples are connected or coupled to one another by a structural element 27 made from a shape-memory material. To illustrate this schematically, a first component 28 and a second component 29 are shown in FIG. 2. These components 28, 29 can be, for example, a connection and a cover part. During use, these two components 28 and 29 are, for example, connected to each other so as to lie closely against each other, such that the component 29, for example, closes the component 28. Under normal circumstances, cleaning these components 28, 29, especially the enclosed space, would involve an increased amount of work. The invention now provides that a structural element 27 is arranged between the two components 28 and 29. This structural element 27 can be a spring made from a shape-memory material. At room temperature, this spring or the structural element 27 has the shape shown schematically in FIG. 2. The second component 29 is connected to the first component 28 via the structural element 27 in such a way that an interior is sealed off. For cleaning, the components 28, 29 are usually fed to a hot atmosphere or a hot liquid. Starting from a certain temperature, the structural element 27 adopts a predetermined shape. In the process, the second component 29 is moved away from the first component 28. For the sake of clarity, a further mechanism that still connects the two components 28 and 29 to each other is not shown here. In this relative positioning of the two components 28, 29 as shown schematically in FIG. 3, the flushing fluid can now also reach the interior of the components 28 and 29, so that the cleaning can be carried out with sufficient thoroughness. As soon as the temperature of the components 28 and 29 cools down to room temperature again, the component 27 deforms back to its original shape, in which the components 28 and 29 bear on top of each other. In this case, the two components 28, 29 can be connected directly to the spring or the structural element 27 or can be movably coupled via a further mechanism (not shown).

Figure 4:
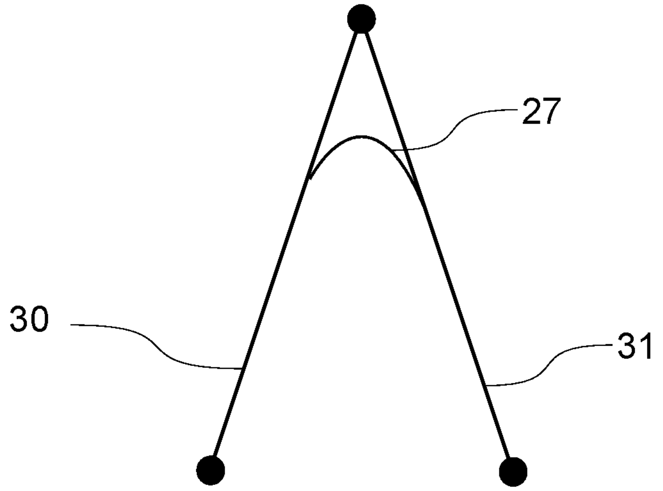
FIG. 4 shows a schematic view of two further components in a basic position.
Figure 5:
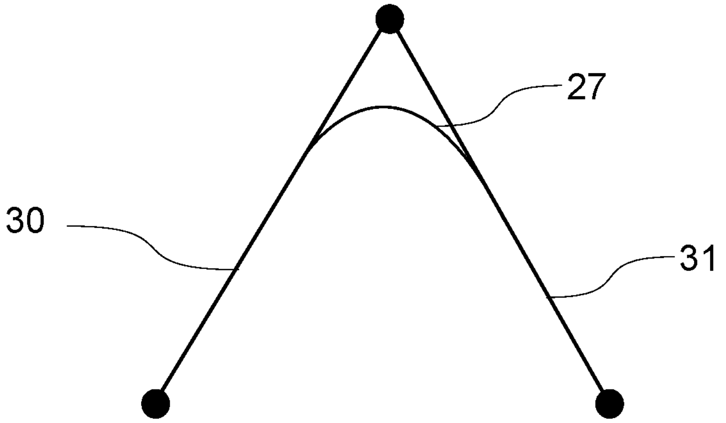
FIG. 5 shows a schematic view of the components according to FIG. 4 in a heated state.

FIGS. 4 and 5 show a further exemplary embodiment of the present invention. In this case, a first spring leg 30 and a second spring leg 31 of the resectoscope 10 shown schematically in FIG. 1 are held in position by a further exemplary embodiment of a structural element 27, which here can be a leaf spring or leg spring. In this case, a basic position or working position of the spring legs 30, 31 is shown in FIG. 4. As soon as said components are heated, the structural element 27 changes its shape and thereby pushes the two spring legs 30 and 31 apart according to FIG. 5. Thus, the components of the resectoscope 10 that are connected to the spring legs 30, 31 are also pushed apart, whereby regions that would otherwise be difficult to access for cleaning are exposed to the cleaning atmosphere or the flushing fluid. Once the cleaning process has been completed or the structural element 27 has cooled down, the latter deforms back to its original position.

In the applications illustrated in FIGS. 2 to 5, the components 28 to 31 are merely heated. Any further intervention by an operator for the purpose of thorough cleaning or sterilization is not necessary. Through the use of the structural element 27 made from the shape-memory material, efficient and thorough cleaning of the components can thus take place. It should be noted again that, according to the invention, such structural elements made from a shape-memory material can be assigned to a plurality of different components of a surgical instrument. The shapes that the structural elements adopt at the appropriate temperature can be adapted according to the type and the degrees of freedom.

LIST OF REFERENCE SIGNS

10 resectoscope
11 working element
12 shaft
13 main body
14 handle unit
15 first grip means
16 second grip means
17 contact body
18 optical guide
19 eyepiece
20 optical guide plate
21 spring element
22 inner tube
23 electrode carrier
24 electrode
25 thumb ring
26 guide
27 structural element
28 first component
29 second component
30 first spring leg
31 second spring leg

The invention claimed is:

1. A handheld surgical instrument comprising:

a first component configured to cover or close an opening in a second component of the handheld surgical instrument, the first component and the second component being movable relative to each other, wherein:

a structural element made from a shape-memory material is arranged between the first component and the second component in order to produce a temperature-dependent relative arrangement of the first component and the second component; and the structural element is configured to be maximally compressed at & characteristic temperature of less than 50° C., and a distance between the first component and the second component is minimal.

2. The handheld surgical instrument as claimed in claim 1, wherein the structural element is a wave spring.

3. The handheld surgical instrument as claimed in claim 1, wherein the structural element is configured to be maximally relaxed at a characteristic temperature of more than 50° C., and a gap is present between the first component and the second component.

4. The handheld surgical instrument as claimed in claim 1, wherein the shape-memory material is nitinol.

5. A handheld surgical instrument comprising:

a first component and a second component, the first component and the second component being movable relative to each other so that the handheld surgical instrument can be brought into different working positions, wherein, the first component and the second component are mechanically coupled to each other by a structural element made from a shape-memory material; and the structural element has a basic shape at a characteristic temperature of less than 50° C. and a relative orientation of the first component and the second component corresponds to a working position.

6. The handheld surgical instrument as claimed in claim 5, wherein the structural element is a spring.

7. The handheld surgical instrument as claimed in claim 5, wherein the structural element, at a characteristic temperature of more than 50° C., is configured to adopt or assume a position or a shape in which a distance between the first component and the second component is smaller or greater than in a starting position.

8. The handheld surgical instrument as claimed in claim 5, wherein the shape-memory material is nitinol.

* * * * *